United States Patent
Witty et al.

(10) Patent No.: US 9,303,032 B2
(45) Date of Patent: *Apr. 5, 2016

(54) 2-(PYRIDIN-2YL)-1, 7-DIAZA-SPIRO [4.4] NONANE-6-ONE COMPOUND AS VOLTAGE-GATED SODIUM CHANNELS MODULATOR

(71) Applicant: CONVERGENCE PHARMACEUTICALS LIMITED, London (GB)

(72) Inventors: David R. Witty, Cambridgeshire (GB); David T. MacPherson, Cambridgeshire (GB); Gerard M. P. Giblin, Cambridgeshire (GB); Steven J. Stanway, Cambridgeshire (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,391

(22) PCT Filed: Dec. 21, 2012

(86) PCT No.: PCT/GB2012/053233
§ 371 (c)(1),
(2) Date: Jun. 13, 2014

(87) PCT Pub. No.: WO2013/093496
PCT Pub. Date: Jun. 27, 2013

(65) Prior Publication Data
US 2014/0350040 A1    Nov. 27, 2014

Related U.S. Application Data

(60) Provisional application No. 61/579,613, filed on Dec. 22, 2011.

(30) Foreign Application Priority Data

Dec. 22, 2011 (GB) .................................. 1122113.2

(51) Int. Cl.
*C07D 487/10* (2006.01)
*C07D 471/10* (2006.01)

(52) U.S. Cl.
CPC ............ *C07D 471/10* (2013.01); *C07D 487/10* (2013.01)

(58) Field of Classification Search
CPC ..................................................... C07D 487/10
USPC ............................................ 546/15; 514/278
See application file for complete search history.

(56) References Cited

U.S. PATENT DOCUMENTS

| 7,655,693 | B2 | 2/2010 | Alvaro et al. |
| 7,803,833 | B2 | 9/2010 | Alvaro et al. |
| 7,855,218 | B2 | 12/2010 | Alvaro et al. |
| 8,093,268 | B2 | 1/2012 | Alvaro et al. |
| 8,143,306 | B2 | 3/2012 | Alvaro et al. |
| 8,153,623 | B2 | 4/2012 | Alvaro et al. |
| 8,153,681 | B2 | 4/2012 | Alvaro et al. |
| 8,759,542 | B2 | 6/2014 | Zajac |
| 2009/0318530 | A1 | 12/2009 | Alvaro et al. |
| 2009/0326032 | A1 | 12/2009 | Alvaro et al. |
| 2010/0105688 | A1 | 4/2010 | Alvaro et al. |
| 2010/0130583 | A1 | 5/2010 | Alvaro et al. |
| 2015/0119404 | A1 | 4/2015 | Giblin et al. |
| 2015/0166551 | A1 | 6/2015 | Giblin et al. |
| 2015/0225400 | A1 | 8/2015 | Witty et al. |

FOREIGN PATENT DOCUMENTS

| WO | WO-2005/035535 A1 | 4/2005 |
| WO | WO-2007/042240 A1 | 4/2007 |
| WO | WO-2008/090114 A1 | 7/2008 |
| WO | WO-2008/090115 A1 | 7/2008 |

OTHER PUBLICATIONS

Guillory (in Brittain ed.), "Polymorphism in Pharmaceutical Solids," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*

(Continued)

*Primary Examiner* — Patricia L Morris
(74) *Attorney, Agent, or Firm* — Honigman Miller Schwartz and Cohn LLP; Kathryn D. Doyle; Jonathan P. O'Brien

(57) ABSTRACT

The invention relates to spiro derivative of formula (I), to the use of said derivative in treating diseases and conditions mediated by modulation of voltage-gated sodium channels, to compositions containing said derivative and processes for its preparation.

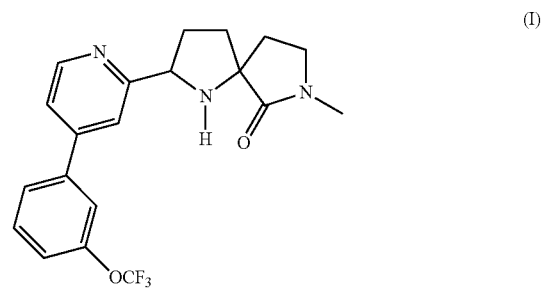

(I)

7 Claims, No Drawings

(56) References Cited

OTHER PUBLICATIONS

Bhattacharya excerpt fr Brittain, H. ed., Polymorphism in Pharmaceutical SolidsDrugs and the Pharmaceutical Sciences ; V. 95 New York Marcel Dekker, Inc., 1999.*

Ivanisevic, I. Pharm. Form. Qual. 2011, pp. 30-33.*

Kirk-Othmer "Crystallization" Encyclopedia of Chem. Tech. v. 8, p. 95-147 (2002).*

Seddon "Pseudopolymorph . . . " Crystal Growth & design v.4(6) p. 1087 (2004) (2 pages from internet).*

Eijkelkamp et al., Neurological perspectives on voltage-gated sodium channels, Brain: A Journal of Neurology, 135, pp. 2585-2612 (2012).*

Large, "The Relationship Between, etc.," Epilepsy Res. 2009; 85(1)96-106.*

* cited by examiner

2-(PYRIDIN-2YL)-1,7-DIAZA-SPIRO [4.4] NONANE-6-ONE COMPOUND AS VOLTAGE-GATED SODIUM CHANNELS MODULATOR

FIELD OF THE INVENTION

The invention relates to spiro derivatives, to the use of said derivatives in treating diseases and conditions mediated by modulation of voltage-gated sodium channels, to compositions containing said derivatives and processes for their preparation.

BACKGROUND OF THE INVENTION

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their state-dependent mechanism of action. The drugs are thought to stabilise an inactivated conformation of the channel that is adopted rapidly after the channel opens. This inactivated state provides a refractory period before the channel returns to its resting (closed) state ready to be reactivated. As a result, state-dependent sodium channel blockers inhibit the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for state-dependent sodium channel blockers is highly conserved between all the subtypes. As a result, drugs such as lidocaine, lamotrigine and carbamazepine do not distinguish between the subtypes.

However, selectivity can be achieved as a result of the different frequencies at which the channels normally operate.

Drugs that block voltage-gated sodium channels in a state-dependent manner are also used in the treatment of bipolar disorder, either to reduce symptoms of mania or depression, or as mood stabilisers to prevent the emergence of mood episodes. Clinical and preclinical evidence also suggests that state-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of state-dependent sodium channel inhibition in key brain areas, such as the frontal cortex. However, interaction with voltage-gated calcium channels may also contribute to the efficacy of these drugs.

WO 2007/042240 (Glaxo Group Limited) describes a series of quaternary alpha-aminocarboxamide derivatives as modulators of voltage-gated sodium channels.

The object of the invention is to identify alternative compounds which modulate voltage-gated sodium channels.

SUMMARY OF THE INVENTION

According to a first aspect of the invention, there is provided a compound of formula (I) which is 7-methyl-2-[4-[3-(trifluoromethoxy)phenyl]-2-pyridyl]-1,7-diazaspiro[4.4]nonan-6-one:

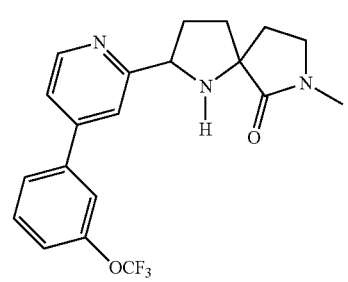

(I)

or a pharmaceutically acceptable salt or solvate thereof.

DETAILED DESCRIPTION OF THE INVENTION

A reference to a compound of formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-aminosalicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment, the compound of formula (I) is: (2R, 5S)-7-Methyl-2-[4-[3-(trifluoromethoxy)phenyl]-2-pyridyl]-1,7-diazaspiro[4.4]nonan-6-one hydrochloride (E1). In an alternative embodiment, the compound of formula (I) is: (2S,5S)-7-Methyl-2-[4-[3-(trifluoromethoxy)phenyl]-2-pyridyl]-1,7-diazaspiro[4.4]nonan-6-one hydrochloride (E3).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof. In a further embodiment, the compound of formula (I) is: (2R,5S)-7-Methyl-2-[4-[3-(trifluoromethoxy)phenyl]-2-pyridyl]-1,7-diazaspiro[4.4]nonan-6-one hemisulfate hydrate (E2).

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention.

Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

In one embodiment, the invention provides compounds of any one of formulae (Ia)-(Id):

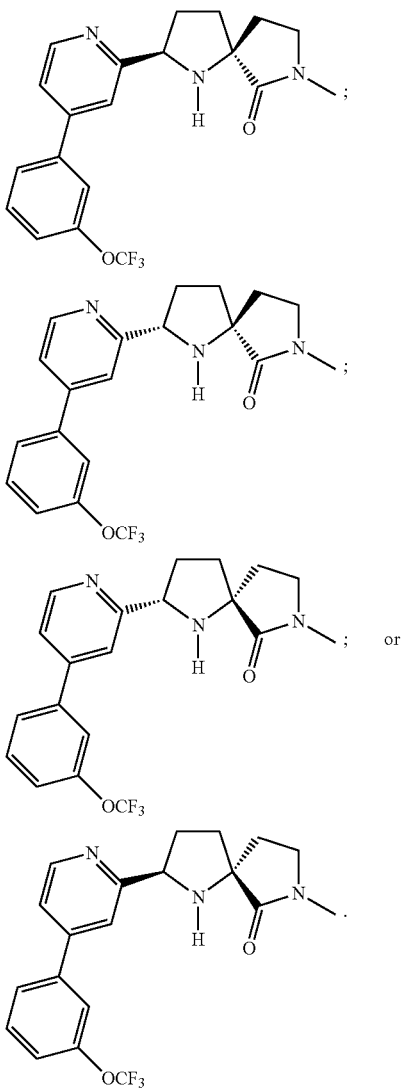

(Ia); (Ib); (Ic); (Id)

In a further embodiment, the invention provides compounds of formula (Ia). Representative examples of compounds of formula (Ia) include Examples 1 and 2 described herein.

In an alternative embodiment, the invention provides compounds of formula (Ib). Representative examples of compounds of formula (Ib) include Example 3 described herein.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, fluorine, such as $^{18}F$, nitrogen, such as $^{13}N$ and $^{15}N$, oxygen, such as $^{15}O$, $^{17}O$ and $^{18}O$.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

According to a further aspect of the invention there is provided a process for preparing a compound of formula (I) as herein defined which comprises:

(a) reacting a compound of formula (II):

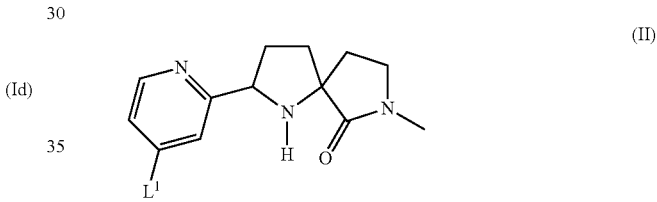

(II)

or a protected derivative thereof, wherein $L^1$ represents a suitable leaving group such as a halogen atom (e.g. bromine) or an —O—SO$_2$CF$_3$ group, with a compound of formula (III):

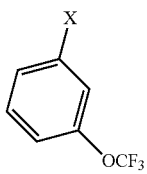

(III)

wherein X represents boronic acid;

(b) reduction of a compound of formula (IV):

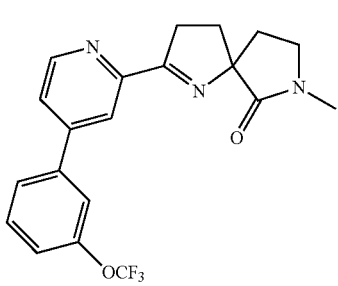

(IV)

or a protected derivative thereof;

(c) deprotection of a protected derivative of a compound of formula (I);

(d) optional formation of a pharmaceutically acceptable salt of a compound of formula (I).

When L¹ represents an —O—SO₂CF₃ group, process (a) typically comprises a Suzuki coupling reaction in the presence of a suitable catalyst such as a Palladium catalyst and a suitable base such as potassium carbonate in a suitable solvent such as aqueous 1,4-dioxane.

When L¹ represents a halogen atom such as bromine, process (a) typically comprises a Suzuki coupling reaction in the presence of a suitable catalyst such as a palladium tetrakis triphenylphosphine and a suitable base. It is recognised that alternative aryl coupling protocols can be used in place of a Suzuki reaction, for example a Stille coupling.

Process (b) typically comprises the use of suitable reducing agents such as sodium triacetoxyborohydride, in the presence of a suitable acid (such as HCl), borane or a modified borane such as tertiarybutylamine:borane complex, or hydrogenation over a suitable catalyst such as platinum.

Compounds of formula (II) may be prepared in accordance with Scheme 1:

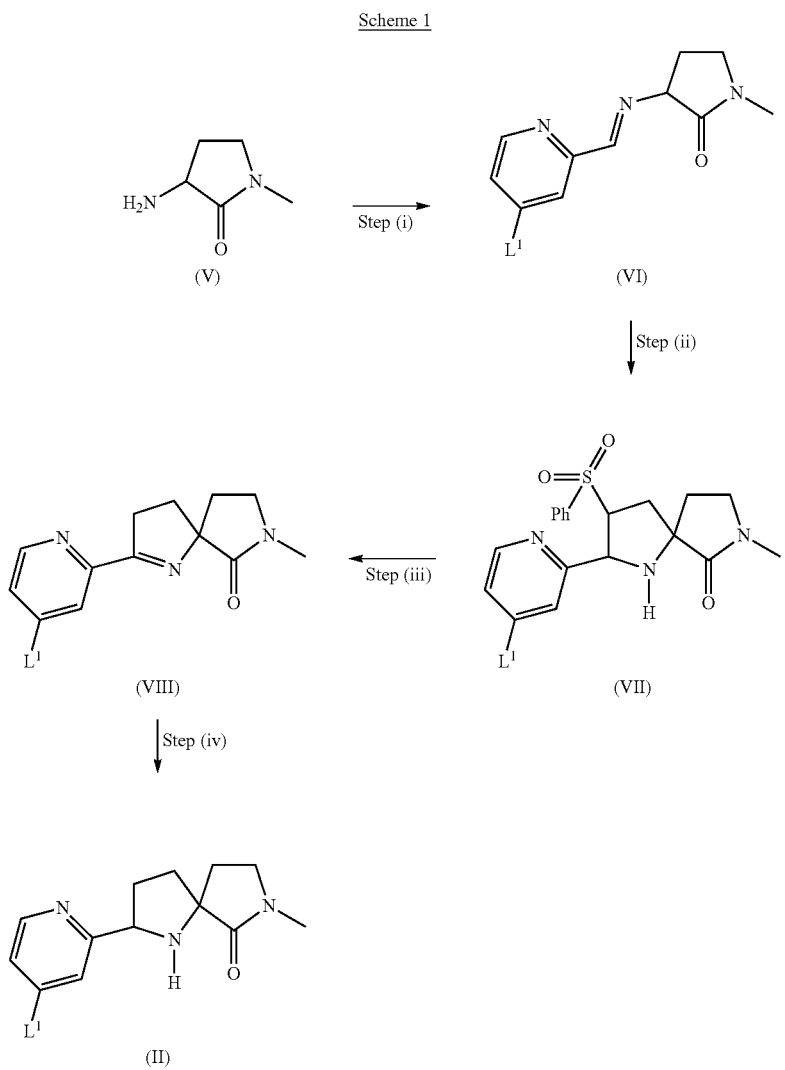

Scheme 1 wherein L¹ represents a suitable leaving group such as a halogen atom (e.g. bromine) or an —O—SO₂—CF₃ group.

Step (i) typically comprises condensation of a compound of formula (V) with a suitable carboxyaldehyde compound in the presence of a dehydrating agent such as magnesium sulfate in a solvent such as dichloromethane.

Step (ii) typically comprises a [3+2] cycloaddition reaction with phenyl vinyl sulfone catalysed by a transition metal salt such as a silver or copper salt (e.g. silver acetate) or a lewis acid (such as calcium triflate), typically in the presence of a base and optionally a chiral phosphine ligand such as 1-(di (1-naphthenyl)phosphinyl)-2-((4S)-4-(propan-2-yl)-4,5-dihydro-1,3-oxazolyl)-ferrocene.

Step (iii) typically comprises elimination of the phenyl sulfone with a strong base such as potassium tert-butoxide.

Step (iv) typically comprises reduction of the imine using a hydride donor such as sodium borohydride or sodium triacetoxyborohydride in the presence of a suitable acid (such as HCl), borane or a modified borane (such as tertiarybutylamine:borane complex), or hydrogenation over a suitable catalyst such as platinum.

Compounds of formula (IV) may be prepared in accordance with Scheme 2:

wherein $P^1$ and $P^2$ represent suitable nitrogen protecting groups.

Step (i) comprises the N-protection of the amino group of amide (V) by for example reaction with an imine such as benzophenone imine in a suitable solvent such as DCE.

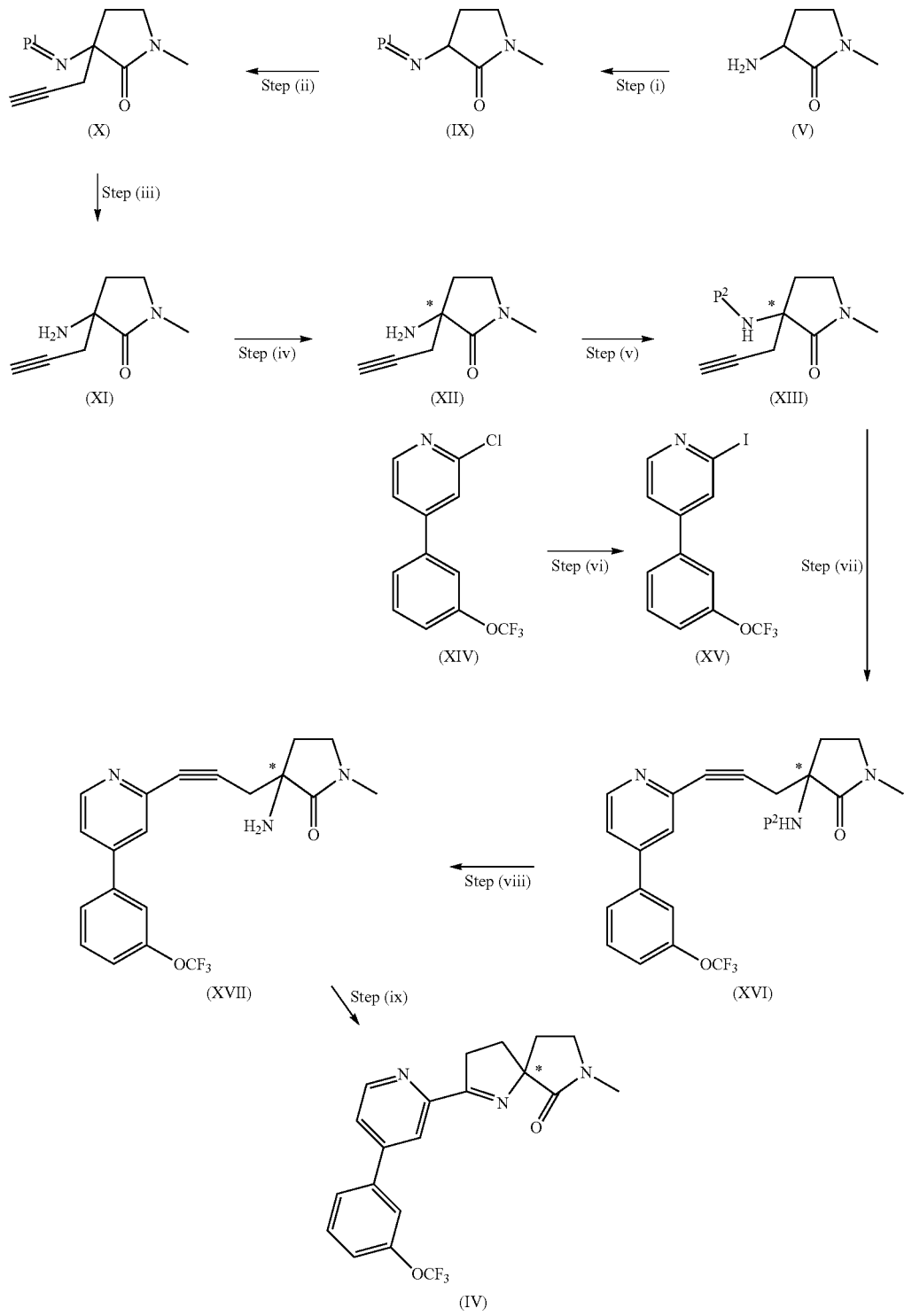

Step (ii) comprises reaction with a propargylating agent such as propargyl bromide in the presence of a base such as potassium tert-butoxide in a suitable solvent such as THF.

Step (iii) comprises the removal of the N-protecting group which may typically be achieved by treatment with a mild acid (such as citric acid) in a suitable solvent such as THF.

Step (iv) comprises a chiral resolution step in which the amine (XI) is formed into a chiral salt by fractional crystallisation of a co-solution with a chiral acid (for example (2S)-2-(6-methoxy-2-naphthyl)propanoic acid or (+)-mandelic acid) from an appropriate solvent (for example acetonitrile, THF or IPA), followed by liberation of the resolved amine by treatment with a base such as a basic ion exchange resin.

Step (v) comprises protection of the amino nitrogen, which can be achieved, for example by introducing a Boc group by treatment of the amine with Boc anhydride.

Step (vi) comprises the conversion of a substituted 2-chloropyridine to a 2-iodopyridine which may typically be achieved by treatment with concentrated aqueous HI solution or by using sodium iodide in acetyl chloride.

Step (vii) comprises a Sonogashira coupling which typically uses a copper catalyst such as copper iodide, a palladium catalyst (for example $PdCl_2(Ph_3P)_2$) and frequently includes an amine base such as diethylamine or diisopropylamine, in a suitable solvent such as THF, DCE, acetonitrile or tert-butyl dimethyl ether.

Step (viii) is an acid catalysed deprotection step which is typically achieved by treatment with trifluoroacetic acid, formic acid or sulphuric acid in a suitable solvent such as dichloromethane, 1,4-dioxane, THF or water.

Step (ix) is typically achieved by treatment with a silver or gold salt such as silver triflate in a solvent such as acetonitrile.

Compounds of formula (III), (V) and (XIV) are either known or may be prepared in accordance with known methodologies.

It will be appreciated by those skilled in organic synthesis that two or more chemical steps in the schemes above may be run sequentially without isolation of intermediate materials.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology. It is also recognised that it may be beneficial to temporarily form a protected derivative of an intermediate in the synthesis, for example, a Boc-protected amine, in order to facilitate chromatographic separation, chiral resolution or to give improved solubility or yields in particular steps.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

An aldehyde or ketone group may be protected, for example, as an acetal ($R—CH(OR)_2$) or ketal ($R_2C(OR)_2$), respectively, in which the carbonyl group (>C=O) is treated with, for example, a primary alcohol. Alternatively, the aldehyde or ketone group is readily regenerated by hydrolysis using an excess of water in the presence of acid.

An amine group may be protected, for example, as an amide (—NRCO—R) or a carbamate (—NRCO—OR), for example, as: a methyl amide (—NHCO—$CH_3$); a benzyl carbamate (—NHCO—$OCH_2C_6H_5$, —NH-Cbz or NH—Z); as a t-butyl carbamate (—NHCO—$OC(CH_3)_3$, —NH-Boc); a 2-biphenyl-2-propyl carbamate (—NHCO—$OC(CH_3)_2C_6H_4C_6H_5$, —NH-Boc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH-Psec).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

Additionally amines may be protected as imines, including substituted benzylimines and benzhydrylimines.

As discussed hereinabove, it is believed that compounds of the invention may be useful for the treatment of diseases and conditions mediated by modulation of voltage-gated sodium channels.

In one embodiment, the compounds will be state-dependent sodium channel inhibitors.

In another embodiment, the compounds will be subtype selective NaV1.7 sodium channel state-dependent inhibitors.

In another embodiment, the compounds will be state-dependent sodium channel inhibitors which have a suitable developability profile on oral administration, for example in terms of exposure (Cmax) and/or bioavailability.

In one embodiment, the compounds will be sodium channel inhibitors.

In another embodiment, the compounds will be subtype selective NaV1.7 sodium channel inhibitors.

In another embodiment, the compounds will be sodium channel inhibitors which have a suitable developability profile on oral administration, for example in terms of exposure (Cmax) and/or bioavailability.

According to a further aspect of the invention, there is provided compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

In one particular embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis and myocardial ischemia.

In one embodiment, the compounds of the invention are useful in the treatment of neuropathic pain or inflammatory pain as described herein.

Without wishing to be bound by theory, other diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-lnduced Mood Disorder, Sedative-, Hypnotic-, or Anxiolytic-lnduced Anxiety Disorder Sedative-, Hypnotic-, or Anxiolytic-lnduced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vii) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

viii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

ix) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

x) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and xi) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xii) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease). The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When used in the treatment or prophylaxis of pain, the compound of formula (I) or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO 99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. Nos. 5,474,995, 5,633,272, 5,466,823, 6,310,099 and 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:

i) A compound of the invention for use in treating or preventing a disease or condition mediated by modulation of voltage-gated sodium channels.

ii) A method of treatment or prevention of a disease or condition mediated by modulation of voltage-gated sodium channels in a mammal comprising administering an effective amount of a compound of the invention.

iii) Use of a compound of the invention in the manufacture of a medicament to treat or prevent a disease or condition mediated by modulation of voltage-gated sodium channels.

iv) Use of a compound of the invention to treat or prevent a disease or condition mediated by modulation of voltage-gated sodium channels.

Examples

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocentres within the spiro fused compounds prepared from achiral starting materials and resolved by use of chiral chromatography have been assigned using a combination of optical rotation and NMR spectroscopy (for determining the relative stereochemistry of adjacent stereocentres) and relating these to chiral intermediates and final compounds which have had their absolute configurations determined by single crystal X-ray crystallography.

Compounds are named using ACD/Name PRO 6.02 chemical naming software (Advanced Chemistry Development Inc., Toronto, Ontario, M5H2L3, Canada), or using Lexichem's automatic chemical naming software (OpenEye Scientific Software Inc. Santa Fe, N. Mex., USA).

Proton Magnetic Resonance (NMR) spectra are typically recorded on a Bruker instruments at 300, 400 or 500 MHz. Chemical shifts are reported in ppm (δ) using the residual solvent line as internal standard. Splitting patterns are designed as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one is reported.

LC-MS Data (LC-MS) is typically generated on an Waters ZQ Mass Spectrometer, operating in switched ES+ and ES− ionization modes coupled to an Agilent 1100 Series HPLC system with in line Aglient 1100 UV-DAD and Sedere SEDEX 75 ELSD Detection. Instrument control and data acquisition is mediated through the Waters MassLynx—OpenLynx software suite. Separation was performed on a Waters SunFire C18 (30×4.6 mm, 3.5 μm) column Flow Rate: 3.0 mL/min. column temperature 30° C. Injection Volume: 5.0 μL. Mobile phase [A]: 3:97:0.05 (v/v/v) Acetonitrile: Water: Formic Acid. Mobile Phase [B]: 97:3:0.05 (v/v/v) Acetonitrile: Water: Formic Acid. Gradient: 97% [A] 3% [B] for 0.1 min. Ramp to 3% [A] 97% [B] at 4.0 min. Hold at 97% [B] to 5 min. Return to 97% [A] at 6 min. Detector parameters: UV-DAD: Range 190 to 450 nm, Interval 2 nm, Threshold 0.1 mAU. ELSD: Temperature 40° C., Range 8. Mass Spectrometer: ES+: Mass Range 125 to 625 in 0.50 sec. Interscan delay 0.25 sec. Capillary 4.0 kV. ES−: Mass Range 125 to 625 in 0.50 sec. Interscan delay 0.25 sec. Capillary 3.0 kV.

In the mass spectra only one peak in the molecular ion cluster is usually reported.

For reactions involving microwave irradiation, a Biotage Initiator was used.

Chiral chromatography was typically performed using a ChiralPak™ AD-H or ChirakPak IA column from Daicel® using heptane/ethanol or heptane/ethanol/methanol mixtures as eluent. Analytical chiral HPLC was carried out either on an Agilent 1100 series HPLC system or on a Gilson HPLC system using a 250×4.6 mm column and a flow rate of 1 ml/min. Preparative chiral HPLC was carried out using a Gilson preparative HPLC system on a 250×19 mm semi-preparative column with a flow rate of 18 ml/min.

Flash silica gel chromatography was carried out on silica gel 230-400 mesh (supplied by Merck AG Darmstadt, Germany) or over pre-packed Biotage silica or NH silica cartridges.

Optical rotations were measured using an Optical Activity Ltd AA-10 automatic polarimeter (Cambridge, UK) using a cell of 10 cm path length and in chloroform solution unless otherwise indicated.

SCX cartridges are ion exchange solid phase extraction columns supplied by Varian. The eluent used with SCX cartridges is methanol followed by 0.2-2.0 M ammonia solution in methanol.

In most preparations, purification was performed using Biotage automatic flash chromatography (SP4 or Isolera) systems.

The following abbreviations are used herein:
Boc tertButyloxycarbonyl
CBz Benzyloxycarbonyl
DCE 1,2-dichloroethane
DCM Dichloromethane
EtOAc Ethyl Acetate
Et$_2$O Ether
HCl Hydrochloric Acid
HPLC High-performance liquid chromatography
K$_2$CO$_3$ Potassium carbonate
LC-MS Liquid chromatography-Mass spectrometry
mCPBA Metachloroperbenzoic acid
MeCN Acetonitrile
MeOH Methanol
MgSO$_4$ Magnesium sulfate
Na$_2$CO$_3$ Sodium carbonate
PdCl$_2$(Ph$_3$P)$_2$ Bis(triphenylphosphine)palladium(II) chloride
THF Tetrahydrofuran Description 1: 3-[(E)-(4-Bromo-2-pyridyl)methyl-eneamino]-1-methyl-pyrrolidin-2-one (D1)

To a stirred solution of 4-bromopyridine-2-carbaldehyde (2232.1 mg, 12 mmol) in anhydrous DCM (60 mL) under nitrogen at room temperature, was added racemic 3-amino-1-methyl-pyrrolidin-2-one (1506.8 mg, 13.2 mmol) [CAS: 2483-65-0] and magnesium sulfate (4500 mg, 37.4 mmol). The resulting mixture was left to stir at room temperature overnight. It was filtered and the filtrate washed with half saturated brine. The organic layer was dried (Na$_2$SO$_4$) and evaporated to give 3-[(E)-(4-bromo-2-pyridyl)methylene-amino]-1-methyl-pyrrolidin-2-one (D1) (3.15 g, 11.2 mmol, 93% yield), as a cream solid;

300 MHz $^1$H NMR δ$_H$ (CDCl$_3$) 2.30-2.41 (1H, m), 2.41-2.55 (1H, m), 2.94 (3H, s), 2.46 (1H, dt), 3.60 (1H, ddd), 4.20 (1H, t), 7.50 (1H, d), 7.21 (1H, s), 8.48 (1H, s), 8.49 (1H, d).

Description 2: 3-(Benzenesulfonyl)-2-(4-bromo-2-pyridyl)-7-methyl-1,7-diazaspiro[4.4]nonan-6-one (D2)

A mixture of 3-[(E)-(4-bromo-2-pyridyl)methylene-amino]-1-methyl-pyrrolidin-2-one (which may be prepared as described in Description 1) (564.3 mg, 2 mmol) and phenyl vinyl sulfone (339.8 mg, 2.02 mmol) in THF (10 mL) was treated with silver acetate (333.99 mg, 2 mmol). The mixture was stirred at room temp for 2 hours, filtered through Celite and concentrated to give the title compound (D2) as a brown gum;

M/Z: 450, 452 (M+H$^+$)

Description 3: (5R)-2-(4-Bromo-pyridin-2-yl)-7-methyl-1,7-diaza-spiro[4.4]non-1-en-6-one (D3R) and (5S)-2-(4-Bromo-pyridin-2-yl)-7-methyl-1,7-diaza-spiro[4.4]non-1-en-6-one (D3S)

Method A

A mixture of 3-(benzenesulfonyl)-2-(4-bromo-2-pyridyl)-7-methyl-1,7-diazaspiro[4.4]nonan-6-one (which may be prepared as described in Description 2) (900.7 mg, 2 mmol) in THF (10 mL) under nitrogen at 0° C. was treated with potassium tert-butoxide in THF (2.94 mL, 5 mmol) portionwise over 10 minutes. The mixture was stirred at 0° C. for 1 hour and then acetic acid (0.29 mL, 5 mmol) was added and the mixture was filtered through Celite and then concentrated. Chromatography of the crude material on a Si—NH column (0-80% ethyl acetate in isohexane) gave 329 mg of a racemic mix of the title compounds as cream solid.

300 MHz $^1$H NMR δ$_H$ (CDCl$_3$) 1.89-1.96 (1H, m), 2.13-2.23 (1H, m), 2.44 (1H, ddd), 2.58 (1H, ddd), 2.97 (3H, s), 3.20-3.44 (3H, m), 3.66-3.74 (1H, m), 7.70 (1H, d), 8.85 (1H, s), 8.97 (1H, d).

This was separated into two enantiomers by chiral chromatography using a ChiralPak AD-H column eluting with 15% ethanol in heptanes. The optical rotation of the isomers is based on analysis of separately purified samples;

Fast isomer: (R)-2-(4-Bromo-pyridin-2-yl)-7-methyl-1,7-diaza-spiro[4.4]non-1-en-6-one (D3R)

Optical rotation α[D/22]=+86.9 (c=1, CHCl$_3$).

Slow isomer: (S)-2-(4-Bromo-pyridin-2-yl)-7-methyl-1,7-diaza-spiro[4.4]non-1-en-6-one (D3S)

Optical rotation α[D/22]=+85.8 (c=1, CHCl$_3$)

Method B

To a stirred solution of 3-[(E)-(4-bromo-2-pyridyl)methyleneamino]-1-methyl-pyrrolidin-2-one (which may be prepared as described in Description 1) (8.1 g, 28.709 mmol) in anhydrous THF (80 mL) under nitrogen at room temperature, was added phenyl vinyl sulfone (4.926 g, 29.283 mmol) and silver acetate (0.53 g, 3.18 mmol) The resulting mixture was left to stir at room temperature for 1.5 hours. The reaction mixture was filtered through Celite and the filtrate was stirred under nitrogen in an ice bath and treated with potassium t-butoxide (33.78 mL of 1.7 M solution in THF, 57.42 mmol) over 5 minutes. After completion of the addition, the mixture was stirred at room temperature for 1 hour, acetic acid (3.29 mL, 57.42 mmol) was added and the mixture was stirred for 5 minutes and then filtered through Celite and concentrated. Chromatography (Biotage Si—NH column, 10-100% ethyl acetate in isohexane) followed by trituration of the isolated product with ether and drying under vacuum gave the title compounds as an off-white solid 5.74 g (racemic). Purification as in Method A gave the separate enantiomers.

Description 4: (2R,5S)-2-(4-Bromo-2-pyridyl)-7-methyl-1,7-diazaspiro[4.4]nonan-6-one (D4R) and (2S,5S)-2-(4-Bromo-2-pyridyl)-7-methyl-1,7-diazaspiro[4.4]nonan-6-one (D4S)

To a stirred solution of (5S)-2-(4-bromo-pyridin-2-yl)-7-methyl-1,7-diaza-spiro[4.4]non-1-en-6-one (which may be prepared as described in Description 3)(1.08 g 3.5 mmol) in anhydrous DCM (18 mL) under nitrogen at room temperature, was added conc. HCl (0.37 mL, 3.68 mmol) and after 5 minutes sodium triacetoxyborohydride (2226.21 mg, 10.5 mmol). The resulting mixture was left to stir at room temperature for 1 hour. Saturated Na$_2$CO$_3$ solution was added (approximately 3 mL) and the mixture was stirred for 10 minutes. The solvents were evaporated and DCM was added and the solution was dried with Na$_2$SO$_4$ and filtered and evaporated to give a yellow oil (approximately 1.1 g) which was purified by flash chromatography on KP—NH silica (0-100% ethyl acetate in isohexane) to give 614 mg of predominantly trans isomer (D4R) and 379 mg of an approximately 6:1 mixture of the cis isomer (D4S) and trans isomer. The trans isomer was further purified by preparative chiral HPLC. Characterisation based on separately purified isomers gave trans isomer (2R,5S)-2-(4-bromo-2-pyridyl)-7-methyl-1,7-diazaspiro[4.4]nonan-6-one (D4R);

300 MHz $^1$H NMR δ$_H$ (CDCl$_3$) 1.82-1.95 (2H, m), 2.00-2.24 (3H, m), 2.5 (1H, br s), 2.47-2.59 (1H, m), 2.90 (3H, s), 3.26-3.37 (2H, m), 4.68 (1H, t), 7.32 (1H, d), 7.75 (1H, s), 8.34 (1H, d). Cis isomer (2S,5S)-2-(4-bromo-2-pyridyl)-7-methyl-1,7-diazaspiro[4.4]nonan-6-one (D4S); 300 MHz $^1$H NMR δ$_H$ (CDCl$_3$) 1.76-1.87 (1H, m), 1.99-2.20 (4H, m), 2.29-2.40 (1H, m), 2.8 (1H, br s), 2.90 (3H, s), 2.28-3.41 (2H, m), 4.38 (1H, t), 7.33 (1H, d), 7.75 (1H, s), 8.38 (1H, d).

Description 5: 3-(Benzhydrylidene-amino)-1-methyl-pyrrolidin-2-one (D5)

Benzophenone imine (200.04 g, 1103.8 mmol) was added dropwise over 20 minutes to a stirred solution of 3 amino-1-methylpyrrolid-2-one (120 g, 1051.2 mmol) in DCE (1000 mL) at ambient temp under nitrogen in a 2 L flask fitted with a magnetic stirrer bar. The reagent was washed with further DCE (100 mL). The stirred solution was heated at reflux on a heat-on block at a block temp of 95° C. for 7 h, using a N$_2$ bubbler with exhaled gas passing through a safety trap then into 2 L of water via an upturned funnel (for scrubbing NH$_3$ gas, estimated to be approx 23 L). The reaction was left to stand at ambient temp overnight under N$_2$. The mixture was evaporated to a thick, off-white oil. To this was added Et$_2$O (700 ml) and to this stirred solution, as it began to crystallize, was added iso-hexane (700 ml) over 2 minutes. The mixture was stirred for 1 h then filtered under suction and washed with Et$_2$O/iso-hexane (1:1) (500 ml). The white solid was dried at 35° C. under vacuum for 3 h to afford 3-(benzhydrylideneamino)-1-methyl-pyrrolidin-2-one (D5) (259.4 g, 88.6%);

300 MHz NMR δ$_H$ (CDCl$_3$) 2.15-2.49 (2H, m), 2.90 (3H, s), 3.26-3.34 (1H, abq), 3.52 (1H, dt), 4.23 (1H, t), 7.30-7.49 (8H, m), 7.63-7.67 (2H, m).

Description 6: 3-(Benzhydrylidene-amino)-1-methyl-3-prop-2-ynyl-pyrrolidin-2-one (D6)

Potassium tert-butoxide 1.7M in THF (602.08 mL, 1023.5 mmol) was added dropwise over a period of 2.5 h to a stirred solution of 3-(benzhydrylidene-amino)-1-methyl-pyrrolidin-2-one (259 g, 930.48 mmol) (which may be prepared as described in Description 5) and 80% solution of propargyl bromide in toluene (124.37 mL, 1116.6 mmol) in 3 A-molecular-sieve-dried reagent grade THF (1900 mL) at −65° C. under nitrogen, in a 5 L flask equipped with an overhead stirrer. After the addition was complete, the mixture was stirred at −65° C. for a further 1 h. The cooling bath was removed and a saturated solution of NaHCO$_3$ (140 ml) was added over 1 minute (at −60° C.). After a further 5 mins more sat NaHCO$_3$ solution (1.4 L) was added followed by Et$_2$O (1.4 L). The mixture was stirred for 1 h then transferred to a separating funnel and water (1.4 L) was added to dissolve all solids. The layers were separated and the aqueous further extracted with Et$_2$O (2×1 L). The combined organic extracts were re-washed with sat. brine (700 ml), diluted with water (700 ml). The organic layer was dried (MgSO$_4$) and evaporated to a volume of approx. 500-600 ml whereupon crystallization started to occur. To this stirred mixture was then added iso-hexane (1.6 L). After standing for 15 mins the cream solid was filtered under suction and washed with iso-hexane (500 ml) and dried at 50° C. under vacuum for 5 h. This afforded 3-(benzhydrylidene-amino)-1-methyl-3-prop-2-ynyl-pyrrolidin-2-one (D6) (274 g, 93%). This was pure by NMR but contains some additional water;

300 MHz NMR δ$_H$ (CDCl$_3$) 1.95 (1H, t), 2.14-2.24 (1H, m), 2.44 (3H, s), 2.45-2.64 (2H, m), 2.94 (2H, t), 3.11 (1H, dt), 7.23-7.48 (8H, m), 7.55-7.59 (2H, m).

Description 7 (3S)-3-Amino-1-methyl-3-prop-2-ynyl-pyrrolidin-2-one (D7S) and (3R)-3-Amino-1-methyl-3-prop-2-ynyl-pyrrolidin-2-one (D7R)

Method A

To a stirred solution of 3-(benzhydrylideneamino)-1-methyl-3-prop-2-ynyl-pyrrolidin-2-one (274 g, 865.99 mmol)

(which may be prepared as described in Description 6) in a 5 L flask equipped with an overhead stirrer, in THF (2.7 L) was added citric acid monohydrate (363.96 g, 1732 mmol) in one portion. The solution was stirred at room temperature for 18 h, giving a thick white precipitate with some sticky solid adhering to the sides of the flask. This sticky solid was loosened with a spatula, then diethyl ether (1.3 L) was added and rapid stirring was continued for a further 1 h. The solid was then filtered under suction and washed efficiently with $Et_2O$ (2×1 L) and dried at 50° C. under vacuum for 3 hours. This produced 268 g of material. This was recrystallized from hot MeOH (1.9 L); hot solution was filtered under suction to give a clear pale yellow solution. The solution was left to stand for 1 h and $Et_2O$ (3 L) was added with stirring. After standing for a further 1 h, the mixture was filtered and washed with MeOH:$Et_2O$ (1:2) (1 L) and the solid pressed dry and further dried at 50° C. under vacuum for 6 hours to afford 312 g of the citrate salt, contaminated with methanol. In a separate container, Ambersep 900 (OH) ion exchange resin (2.31 kg, 2722 7 mmol) was stirred for 5 minutes with MeOH (2 L) to pre-wash the resin. The suspended resin was filtered under suction and the moist pre-washed resin was added to a stirred suspension of the previously prepared citrate salt in methanol (3 L) in a 10 L vessel equipped with an overhead stirrer. The mixture was stirred for a total of 1.5 h at ambient temp then filtered under suction. The filtered resin was washed with MeOH (2×1.5 L). The filtrate and washings were evaporated in vacuo to an oil which was redissolved in DCM (1.5 L) and dried ($Na_2SO_4$), filtered, evaporated to a pale yellow oil, which was dried at RT overnight to give 3-amino-1-methyl-3-prop-2-ynyl-pyrrolidin-2-one (D7) (106.9 g, 79.9%);

300 MHz NMR $\delta_H$ (CDCl$_3$) 1.65 (3H, br.s), 1.94-2.05 (2H, m), 2.31-2.39 (1H, m), 2.41-2.55 (2H, m), 2.89 (3H, Me), 3.33-3.39 (2H, m).

A portion of this material (1.75 g, 11.5 mmol) was separated on chiral HPLC using a semi-prep AD-H column, eluting with 20% EtOH/heptane at 18 ml/min. Peaks were identified at 215 nm:

(3S)-3-amino-1-methyl-3-prop-2-ynyl-pyrrolidin-2-one (D7S) 549 mg retention time=13.7 mins (37.5%); Optical rotation α[D/22]=−81.0 (c=0.975, CHCl$_3$);

(3R)-3-amino-1-methyl-3-prop-2-ynyl-pyrrolidin-2-one (D7R) 407 mg retention time=17.9 mins (36.4%); Optical rotation α[D/22]=+78.8 (c=0.965, CHCl$_3$).

Method B: (3S)-3-Amino-1-methyl-3-prop-2-ynyl-pyrrolidin-2-one (D7S)

A controlled lab reactor with heated/cooled jacket and an overhead paddle-stirrer was charged with IPA (2250 mL) and (2S)-2-(6-methoxy-2-naphthyl)propanoic acid (84.72 g, 367.92 mmol) was added. The suspension was stirred and warmed to 75° C. giving a solution. A solution of 3-amino-1-methyl-3-prop-2-ynyl-pyrrolidin-2-one (which may be prepared as described in Description 7 Method A) (55.99 g, 367.92 mmol) in IPA (1100 mL) was then added dropwise over 1.5 hours. The reaction mixture was stirred at 75° C. for 1 hr then cooled to 55° C. over 1 hr. The reaction was seeded with pure (S) isomer salt at every 1 degree drop in temperature until the seed remained out of solution (ca. 71° C.). The reaction mixture crystallised and was stirred at 55° C. for 1 hr. The mixture was then cooled to 40° C. over approximately 20 minutes and filtered under suction into a pre-warmed filter funnel over a fast filter paper. The vessel was rinsed out with IPA (600 mL) pre-warmed to 40° C. and this was used to wash the collected solids. The solids were dried under suction until no more solvent came out and then were dried in a vacuum oven at 50° C. to give a white solid, 59.37 g (3S)-1-methyl-2-oxo-3-prop-2-ynyl-pyrrolidin-3-yl]ammonium (2S)-2-(6-methoxy-2-naphthyl)propanoate. A portion of this material was removed and dissolved in methanol, passed down an SCX column, washed with methanol and then eluted with 0.5M ammonia in methanol. The ammonia elute was evaporated to a pale yellow gum, which was analysed by chiral HPLC (20:80 EtOH:heptane, IA column) showing S-isomer 99.5% and R-isomer 0.5%. Ambersep 900-OH (500 g, 155.24 mmol) was stirred in methanol (1000 mL) for 5 minutes, then filtered and dried under suction until no more liquid came out. The washed resin was added to a stirred suspension of S-isomer salt (59.37 g, 155.24 mmol) in methanol (1000 mL). The mixture was stirred for 1 hr, then filtered. The resin was resuspended in methanol (1000 mL) and stirred for an hour and then filtered. The combined filtrates were evaporated to give a slightly cloudy yellow oil. The oil was dissolved in dichloromethane (ca. 200 mL) and dried over magnesium sulphate, filtered and evaporated to give a clear yellow oil (3S)-3-amino-1-methyl-3-prop-2-ynyl-pyrrolidin-2-one (D7S) (22.729 g). This material was identical spectroscopically to that prepared by chiral chromatography in Method A.

Method C: (3R)-3-Amino-1-methyl-3-prop-2-ynyl-pyrrolidin-2-one (D7R)

Enriched recrystallisation mother liquors containing, for example, a 91:9 ratio of (3R)-3-amino-1-methyl-3-prop-2-ynyl-pyrrolidin-2-one naproxen salt and its (3S) enantiomer, (27 g) (which may be obtained from the fractional crystallisation procedure described in Method B) were evaporated and dissolved in acetonitrile at 30±5° C. The reaction mass was heated to 70±5° C. and stirred for 10 minutes then slowly cooled to 40±2° C. A seed of the R-amine-naproxen salt was introduced and the reaction mixture maintained at 40±2° C. for 1 hr. The reaction mass was cooled to 30±5° C. and filtered. The isolated salt was washed with acetonitrile and dried under vacuum at 47.5±2.5° C. for 6±1 hours to give 18.2 g of the salt with a 99.8% enantiomeric excess of the R isomer. The material was then converted to the free base form as described for the S-enantiomer in Method B to give the title compound (D7R). This material was identical spectroscopically to that prepared by chiral chromatography in Method A.

Description 8: tert-Butyl N-[(3S)-1-methyl-2-oxo-3-prop-2-ynyl-pyrrolidin-3-yl]carbamate (D8)

To a solution of (3S)-3-amino-1-methyl-3-prop-2-ynyl-pyrrolidin-2-one (which may be prepared as described in Description 7) (72.66 g, 477.4 mmol) in DCM (1000 mL) was added a solution of Boc$_2$O (125.03 g, 572.88 mmol) in DCM (700 mL) in one portion. The reaction was then stirred at 40° C. (bath temp. not internal temp.) over 5 hrs, then at room temperature over the weekend. The reaction was concentrated in vacuo, and the residue was suspended in a mixture of $Et_2O$ and isohexane (1:1, 250 mL) and stirred for 30 minutes. The suspension was filtered, and the solid was washed with a mixture of $Et_2O$ and isohexane (1:1, 250 mL), followed by isohexane (3×250 mL). The solid was then dried in a vacuum oven for 2 hours (40° C.) to give a white solid, tert-butyl N-[(3S)-1-methyl-2-oxo-3-prop-2-ynyl-pyrrolidin-3-yl]carbamate (D8) (99.25 g);

300 MHz NMR $\delta_H$ (CDCl$_3$) 1.43 (9H, s), 2.01 (1H, app. t), 2.45-2.59 (3H, m), 2.78, 2.82 (1H, 2×br.s), 2.81 (3H, s), 3.35-3.45 (2H, m), 5.23 (1H, br.s).

A second crop was isolated from the filtrate to give a further batch, 5.535 g of similar purity.

Description 9: 2-Iodo-4-[3-(trifluoromethoxy)phenyl]pyridine (D9)

Acetyl chloride (4.45 mL, 62.6 mmol) was added to a solution of 2-chloro-4-[3-(trifluoromethoxy)phenyl]-pyridine [CAS 1261856-64-7] (11.42 g, 41.73 mmol) and sodium iodide (31.28 g, 208.67 mmol) in MeCN (200 mL) under $N_2$, and the resulting suspension was heated at 80° C. for 18 hrs. Additional sodium iodide was added (20 mol %) and stirring was continued for 3 hrs. The reaction was cooled and the mixture was treated with aqueous sodium carbonate. After 5 minutes, solid sodium metabisulphite was added until decolourisation achieved. Water was added to redissolve a precipitate which had formed. The mixture was diluted with EtOAc and the layers separated. The aqueous layer was washed with EtOAc (2×), the combined organics were dried ($MgSO_4$) and the solvent evaporated to afford the crude 2-iodo-4-[3-(trifluoromethoxy)phenyl]pyridine (D9) (16.3 g) as a amber oil containing about ~5% of reduced 2-H material and ~8% of unreacted chloride starting material;

300 MHz NMR $\delta_H$ (CDCl$_3$) 7.35 (1H, t) 7.42-7.28 (2H, m), 7.52-7.58 (2H, m), 7.95 (1H, s), 8.46 (1H, d).

Description 10: tert-Butyl N-[(3S)-1-methyl-2-oxo-3-[3-[4-[3-(trifluoromethoxy)phenyl]-2-pyridyl]prop-2-ynyl]pyrrolidin-3-yl]carbamate (010)

Copper Iodide (104.92 mg, 0.5500 mmol), followed by PdCl$_2$(Ph$_3$P)$_2$ (193.34 mg, 0.2800 mmol) was added portionwise to a solution of the tert-butyl N-[(3S)-1-methyl-2-oxo-3-prop-2-ynyl-pyrrolidin-3-yl]carbamate (2.78 g, 11.02 mmol) (which may be prepared as described in Description 8), 2-iodo-4-[3-(trifluoromethoxy)-phenyl]pyridine (6.03 g, 16.53 mmol) (which may be prepared as described in Description 9) and Et$_2$NH (5.7 mL, 55.09 mmol) in THF (60 mL) under $N_2$ and the reaction was stirred at 20° C. for 18 hrs. Additional PdCl$_2$(Ph$_3$P)$_2$ (1.25 mol %) and CuI (2.5 mol %) catalyst was added. The reaction was left to stir for 3 days. The solvent was evaporated and the residue was suspended in EtOAc and washed with water/sat. aq. NaHCO$_3$. The organics were collected, dried (Na$_2$SO$_4$) and the solvent evaporated to afford a brown oil. This was purified using a Biotage SP4, with 100 g SNAP cartridge, eluting with 0 to 100% EtOAc in i-hexane. Clean fractions were collected and the solvent evaporated to afford a yellow oil. The remaining fractions were collected and re-columned using a SP4, 100 g SNAP cartridge, 0 to 10% MeOH/EtOAc and the product was collected and combined with the clean material from the first column to afford the tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (D10) (5.38 g, 10.991 mmol, 99.8% yield) as a yellow oil containing some Ph$_3$P residues;

300 MHz NMR $\delta_H$ (CDCl$_3$) 1.45 (9H, s), 2-49-2.72 (2H, m), 2.82 (1H, d), 2.95 (3H, s), 3.11 (1H, d), 3.42 (1H, t), 3.57 (1H, q), 5.31 (1H, br.s), 7.34 (1H, d), 7.43 (1H, d), 7.48 (1H, s), 7.54-7.61 (3H, m), 8.64 (1H, d).

Description 11: (3S)-3-Amino-1-methyl-3-[3-[4-[3-(trifluoromethoxy)phenyl]-2-pyridyl]prop-2-ynyl]pyrrolidin-2-one (D11)

Method A

Trifluoroacetic acid (10 mL, 134.63 mmol) was added to a solution of the tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (which may be prepared as described in Description 10) (5.38 g, 10.99 mmol) in DCM (50 mL) at 20° C. and the reaction was stirred until complete. Solid K$_2$CO$_3$ was added to quench the TFA present and the mixture was diluted with water. The phases were separated and the aqueous layer was washed with dichloromethane (×2). The combined organic layers were dried (MgSO$_4$) and the solvent was evaporated to give the (3S)-3-amino-1-methyl-3-[3-[4-[3-(trifluoromethoxy)phenyl]-2-pyridyl]prop-2-ynyl]pyrrolidin-2-one (D11) (4.78 g, 12.276 mmol, 111.7% yield) as an amber oil containing some Ph$_3$PO;

300 MHz $^1$H NMR $\delta_H$ (CDCl$_3$) 1.82 (2H, br.s), 2.08 (1H, dt), 2.48 (1H, ddd), 2.78 (2H, abq), 2.93 (3H, s), 3.38-3.47 (2H, m), 7.34 (1H, d), 7.43 (1H, dd), 7.47 (1H, s), 7.51-7.62 (3H, m), 8.66 (1H, d).

Method B

A solution of tert-butyl N-[(3S)-1-methyl-2-oxo-3-[3-[4-[3-(trifluoromethoxy)phenyl]-2-pyridyl]prop-2-ynyl]pyrrolidin-3-yl]carbamate (8.91 g, 18.19 mmol) (which may be prepared as described in Description 10) in 1,4-dioxane (70 mL) was cooled in an ice bath and treated dropwise with conc. H$_2$SO$_4$ (7.4 mL, 93.22 mmol). The mixture was allowed to reach room temperature and after 45 mins, the mixture was again cooled in an ice bath and treated cautiously with satd. aq. Na$_2$CO$_3$ solution (~150 ml). The mixture was diluted with ethyl acetate (200 ml) and the product was extracted into ethyl acetate (2×150 ml). The combined organic extracts were dried (Na$_2$SO$_4$) and concentrated to give the title compound (D11) as an orange oil (6.88 g, 97%) consistent spectroscopically with that prepared by Method A.

Description 12: (5S)-7-Methyl-2-[4-[3-(trifluoromethoxy)phenyl]-2-pyridyl]-1,7-diazaspiro[4.4]non-1-en-6-one (D12)

Silver trifluoromethanesulphonate (564.86 mg, 2.2 mmol) was added to a solution of (3S)-3-amino-1-methyl-3-[3-[4-[3-(trifluoromethoxy)phenyl]-2-pyridyl]prop-2-ynyl]pyrrolidin-2-one (which may be prepared as described in Description 11) (4.28 g, 10.99 mmol) in MeCN (60 mL) at 40° C. and the reaction was stirred for 18 hours. Additional AgOTf (10 mol %) was added and stirring was continued for 24 hrs. The solvent was evaporated and the residue was suspended in EtOAc. The organic phase was washed with water, dried (Na₂SO₄) and the solvent evaporated to afford a light brown oil. This was purified using an Isolera, with a (50+100) g SNAP cartridge, eluting with 0 to 100% (mixture of 1% of 2M NH₃ in MeOH; 9% MeOH; 90% EtOAc) in EtOAc affording the (5S)-7-methyl-2-[4-[3-(trifluoromethoxy)phenyl]-2-pyridyl]-1,7-diazaspiro[4.4]non-1-en-6-one (D12) (3.17 g, 8.1414 mmol, 74.1% yield) as a light brown solid;

300 MHz ¹H NMR $\delta_H$ (CDCl₃) 1.95 (1H, ddd), 2.19 (1H, dt), 2.46 (1H, ddd), 2.59 (1H, ddd), 2.97 (3H, s), 3.26-3.49 (3H, m), 6.68 (1H, dt), 7.32 (1H, d), 7.50-7.56 (3H, m), 7.64 (1H, d), 8.36 (1H, s), 8.74 (1H, d).

Description 13 and Description 14: tert-Butyl (2R, 5S)-7-methyl-6-oxo-2-[4-[3-(trifluoromethoxy)phenyl]-2-pyridyl]-1,7-diazaspiro[4.4]nonane-1-carboxylate (D13) and tert-Butyl (2S,5S)-7-methyl-6-oxo-2-[4-[3-(trifluoromethoxy)phenyl]-2-pyridyl]-1,7-diazaspiro[4.4]nonane-1-carboxylate (D14)

Concentrated aqueous hydrochloric acid (698.76 µL, 8.14 mmol) was added to a solution of (5S)-7-methyl-2-[4-[3-(trifluoromethoxy)phenyl]-2-pyridyl]-1,7-diazaspiro[4.4]non-1-en-6-one (which may be prepared as described in Description 12) (3.17 g, 8.14 mmol) in DCM (60 mL) at 0° C. Finally, sodium triacetoxyborohydride (5.18 g, 24.42 mmol) was added in a single portion and the resulting mixture was stirred for 18 hours. The reaction was quenched by the addition of sat. aq. Na₂CO₃ and stirring was continued for 5 mins. The phases were separated, the organic layer was dried (Na₂SO₄) and the solvent was evaporated to afford an amber oil (3.24 g), a 2.3:1 mixture of 2S and 2R isomers of (5R)-7-methyl-6-oxo-2-[4-[3-(trifluoromethoxy)phenyl]-2-pyridyl]-1,7-diazaspiro[4.4]nonane (3.18 g, 8.12 mmol). This was dissolved in DCE (60 mL) and Boc₂O (2.4 g, 11.01 mmol) was added and the reaction was stirred at 40° C. for 3 days. The solvent was evaporated to afford a brown oil. This was purified using Biotage SP4, with a 100 g SNAP cartridge, eluting with EtOAc followed by 0 to 10% MeOH in EtOAc. The first to elute isomer tert-butyl (2S,5S)-7-methyl-6-oxo-2-[4-[3-(trifluoromethoxy)phenyl]-2-pyridyl]-1,7-diazaspiro[4.4]nonane-1-carboxylate (D14) was isolated (1.03 g, 2.0956 mmol, 25.8% yield) and showed rotamers in the NMR spectrum;

300 MHz ¹H NMR $\delta_H$ (CDCl₃) 1.18 1.45 (9H, 2×s), 1.72-1.82 (1H, m), 1.98-2.24 (3H, m), 2.35-2.78 (2H, m), 2.94, 2.98 (3H, 2×s), 3.25-3.55 (2H, m), 5.11, 5.20 (1H, 2×d), 7.22-7.31 (1H, m), 7.35-7.42 (1H, m), 7.50-7.61 (1H, m), 7.66-7.70 (1H, m), 7.79, 7.91 (1H, 2×d), 8.59-8.63 (1H, m), 8.66, 8.87 (1H, 2×s).

The slower isomer tert-butyl (2R,5S)-7-methyl-6-oxo-2-[4-[3-(trifluoromethoxy)phenyl]-2-pyridyl]-1,7-diazaspiro[4.4]nonane-1-carboxylate (D13) (2.85 g, 5.7986 mmol, 71.4% yield) also showed rotamers in the NMR spectrum;

300 MHz ¹H NMR $\delta_H$ (CDCl₃) 1.18, 1.41 (9H, 2×s), 1.95-2.29 (4H, m), 2-54-2.69 (1H, m), 2-79-3.03 (1H, m), 2.91, 2.95 (3H×s), 3.29-3.60 (2H, m), 5.16, 5.32 (1H, 2×dd), 7.29-7.58 (6H, m), 8.62-8.67 (1H, m).

Description 15: tert-Butyl (2S,5S)-7-methyl-6-oxo-2-[4-[3-(trifluoromethoxy)phenyl]-2-pyridyl]-1,7-diazaspiro[4.4]nonane-1-carboxylate (D15)

A solution of crude (2S,5S)-7-methyl-2-[4-[3-(trifluoromethoxy)phenyl]-2-pyridyl]-1,7-diazaspiro[4.4]nonan-6-one (which may be isolated as described in Example 2, Method B) (111 mg, 0.2800 mmol) in DCM (3 mL) containing a proportion of the (2R)-isomer was treated with Boc₂O (0.08 g, 0.3700 mmol) and the mixture was stirred at room temperature overnight. The solvent was evaporated and the residue was purified by chromatography using a Biotage SNAP 10 g cartridge, eluting with ethyl acetate, to give the title compound (D15) as a white solid (124.5 mg).

M/Z: 392 (M+H⁺) 492

Example 1

2R,5S)-7-Methyl-2-[4-[3-(trifluoromethoxy)phenyl]-2-pyridyl]-1,7-diazaspiro[4.4]nonan-6-one hydrochloride (E1

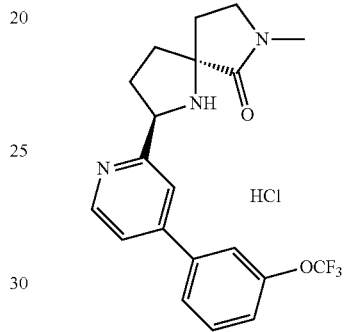

To a solution of (2R,5S)-2-(4-bromo-2-pyridyl)-7-methyl-1,7-diazaspiro[4.4]nonan-6-one (which may be prepared as described in Description 4) (22 mg, 0.0709 mmol) in MeCN (1 mL) and water (0.2000 mL) in a Smith microwave vessel was added [3-(trifluoromethoxy)phenyl]boronic acid (14.605 mg, 0.0709 mmol), bis(triphenylphosphine)palladium (II) dichloride (2.4891 mg, 0.0035 mmol) and sodium carbonate (15.035 mg, 0.1418 mmol). The reaction vessel was sealed and purged with nitrogen. The reaction mixture was heated by microwave at 100° C. for 25 minutes. The reaction mixture was treated with water and was extracted with DCM twice and the organic layers were collected by passing down a PhaseSep cartridge. It was further eluted on an SCX-2 cartridge (0.5 g) and washed with DCM followed by MeOH. The desired product was eluted off the cartridge with ammonia in MeOH (0.2 M). Evaporation of solvents gave an amber oil. It was further purified by preparative HPLC (ChiralPak AD-H) column, eluting with ethanol/n-heptane (1:3) to give the desired product as an amber oil;

300 MHz ¹H NMR $\delta_H$ (CDCl₃) 1.86-2.28 (5H, m), 2.50-2.62 (1H, m), 2.8 (1H, br s), 2.91 (3H, s), 2.25-3.89 (2H, m), 4.77 (1H, t), 7.29 (1H, d), 7.32 (1H, d), 7.48 (1H, t), 7.53 (1H, q), 7.60 (1H, d), 7.70 (1H, s), 8.62 (1H, d).

This was converted to the (2R,5S)-7-methyl-2-[4-[3-(trifluoromethoxy)phenyl]-2-pyridyl]-1,7-diazaspiro[4.4]-nonan-6-one hydrochloride (E1) by addition of HCl (1 M in diethyl ether) to a DCM solution of the free base. Evaporation followed by further drying under reduced pressure gave an amber solid. The latter was further dried under reduced pressure at 40° C. to give the title compound in 58% yield;

M/Z: 392 (M+H⁺).

Example 2

(2R,5S)-7-Methyl-2-[4-[3-(trifluoromethoxy)phenyl]-2-pyridyl]-1,7-diazaspiro[4.4]nonan-6-one hemisulfate (E2)

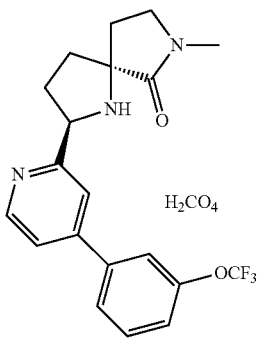

Method A tert-Butyl (2R,5S)-7-methyl-6-oxo-2-[4-[3-(trifluoromethoxy)phenyl]-2-pyridyl]-1,7-diazaspiro[4.4]nonane-1-carboxylate (which may be prepared as described in Description 13) (2.85 g, 5.8 mmol) was added to a solution of 4M HCl in dioxane (10 mL, 40 mmol) in DCM (20 mL) at 20° C. and the reaction stirred for 18 hours. The solvent was evaporated and the residue was suspended in DCM. This was treated with sat. aq. NaHCO$_3$ and the phases separated. The aqueous layer was washed with DCM (3×) and the combined organic layer was dried (Na$_2$SO$_4$) and the solvent evaporated to afford an amber oil (2.32 g). This was purified on a 100 g SNAP cartridge, using 0 to 10% MeOH in EtOAc. desired clean product fractions were collected and the solvent evaporated to afford (2R,5S)-7-methyl-2-[4-[3-(trifluoromethoxy)phenyl]-2-pyridyl]-1,7-diazaspiro[4.4]nonan-6-one as a pale yellow oil identical to that prepared in Example 1. Sulphuric acid (0.26 mL, 4.6 mmol) was added to a solution of this material (1.8 g, 4.6 mmol) in DCM (17 mL) at 20° C. and the reaction stirred for 5 mins. The solvent was evaporated and the residue was dissolved in deionised water. This was freeze dried for 20 hours to give (2R,5S)-7-methyl-2-[4-[3-(trifluoromethoxy)phenyl]-2-pyridyl]-1,7-diazaspiro[4.4]nonan-6-one hemisulfate hydrate (E2) (2.14 g) as a colourless solid;

300 MHz $^1$H NMR $\delta_H$ (MeOD) 2.26-2.49 (4H, m), 2.70 (1H, dt), 2.82-2.91 (1H, m), 2.98 (3H, s), 3.56 (2H, dd), 5.31 (1H, m), 7.46 (1H, d), 7.68 (1H, t), 7.82 (1H, s), 7.77 (1H, dd), 7.83 (1H, d), 7.87 (1H, s), 8.73 (1H, d).

Method B

A solution of (5S)-7-methyl-2-[4-[3-(trifluoromethoxy)phenyl]-2-pyridyl]-1,7-diazaspiro[4.4]non-1-en-6-one (which may be prepared as described in Description 12) (5.77 g, 14.82 mmol) in DCM (75 mL) was cooled to −78° C. under nitrogen and a solution of borane tert-butylamine complex (1.43 g, 16.44 mmol) in DCM (15 ml) was added dropwise maintaining the internal temperature below −70° C. over 10 mins. The mixture was stirred at −78° C. for 90 mins and then the cooling bath was removed and 5M hydrochloric acid (30 mL, 150 mmol) was added via the dropping funnel over 1-2 mins. The mixture was brought to 25-30° C. with a water bath and the mixture stirred vigourously for 30 mins. More DCM (200 ml) was added and the mixture was then slowly poured into a beaker containing sodium carbonate (17.28 g, 163.01 mmol) in water (150 ml) and the mixture was stirred for 10 mins. The layers were separated and the aqueous layer (pH 9) was re-extracted with DCM (2×150 ml). The combined organic layers were washed with brine, dried (Na$_2$SO$_4$) and concentrated to give a yellow gum, a 15:1 mixture of (2R,5S) and (2S,5S) isomers. This mixture was separated by chromatography using a Biotage SNAP 340 g cartridge eluting with 5% of 0.5M methanolic ammonia in ethyl acetate (isocratic) to obtain the major isomer (2R,5S)-7-methyl-2-[4-[3-(trifluoromethoxy)phenyl]-2-pyridyl]-1,7-diazaspiro[4.4]nonan-6-one (5.76 g), increasing to 10% of 0.5M methanolic ammonia to elute the minor (2S,5S)-7-methyl-2-[4-[3-(trifluoromethoxy)phenyl]-2-pyridyl]-1,7-diazaspiro[4.4]nonan-6-one isomer (111 mg) which was contaminated by traces of the (2R,5S) isomer. The (2R,5S) isomer was identical spectroscopically to that prepared in Example 1. This was then converted to the salt form: Sulphuric acid (0.75 mL, 13.48 mmol) was added to a solution of (2R,5S)-7-methyl-2-[4-[3-(trifluoromethoxy)phenyl]-2-pyridyl]-1,7-diazaspiro[4.4]nonan-6-one (5.27 g, 13.48 mmol) in DCM (70 mL) at 20° C. and the reaction stirred for 5 mins. The solvent was evaporated and the residue was triturated with diethyl ether and dried. This solid (approx. 6 g) was dissolved in acetone (30 ml) and then added dropwise to diethyl ether (600 ml) with rapid stirring.

The mixture was stirred for 10 mins and then the solid was collected by filtration and dried in a vacuum oven at 50° C. overnight. The solid was dissolved in deionised water (~60 ml), filtered and freeze dried and then dried in a vacuum oven at 50° C. for 3 hrs. To give the title material (E2) as a beige solid, (5.9 g) identical spectroscopically to that prepared by method A.

Example 3

2S,5S)-7-Methyl-2-[4-[3-(trifluoromethoxy)phenyl]-2-pyridyl]-1,7-diazaspiro[4.4]nonan-6-one hydrochloride (E3

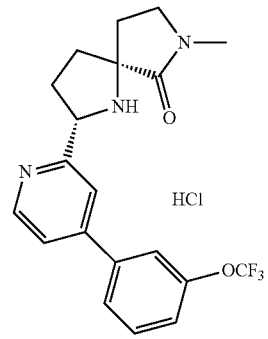 [SMILES: CN1CC[C@@]2(CC[C@@H](c3cc(-c4cccc(OC(F)(F)F)c4)ccn3)N2)C1=O ; Cl]

A solution of tert-butyl (2S,5S)-7-methyl-6-oxo-2-[4-[3-(trifluoromethoxy)phenyl]-2-pyridyl]-1,7-diazaspiro[4.4]nonane-1-carboxylate (which may be prepared as described in Description 15) (124.5 mg, 0.2500 mmol) in HCl in dioxan (3 mL, 12 mmol) was allowed to react at room temperature for 2 hrs. The solvent was evaporated and the residue was dissolved in methanol and passed through an SCX cartridge, washed with methanol and the product eluted with 0.5M NH$_3$ in methanol to give the free base as a clear gum (97 mg); 300 MHz $^1$H NMR $\delta_H$(CDCl$_3$) 1.83-1.89 (1H, m), 2.13-2.21 (4H, m), 2.40 (1H, m), 2.9 (1H, br.s), 2.94 (3H, s), 3.30-3.43 (2H, m), 4.50 (1H, t), 7.31 (1H, d), 7.37 (1H, d), 7.53 (2H, t), 7.64 (1H, d), 7.87 (1H, s), 8.64 (1H, d).

A solution of this material in DCM (2 mL) was treated with HCl in ether (0.27 mL, 0.2700 mmol) and the mixture was allowed to stand at room temp for 2 minutes. The solvent was evaporated almost to dryness and then diethyl ether (20 ml) was added to precipitate the product. The solid was collected by filtration and then dried in the vacuum oven overnight at 45° C. to afford the title compound (E3) (84 mg);

M/Z: 392 (M+H$^+$).

Biological Assays

The compounds of the invention were tested in a QPatch NaV1.7 assay.

QPatch NaV1.7 Assay

HEK293-hNaV1.7 cells were grown in DMEM-F12+10% FBS culture media at 37° C. At a confluency of 50-70% cells were dissociated from culture flasks & triturated to ensure unicellular cell suspension; cell density was measured & adjusted to 2-3×10$^6$ cells/ml. Recordings were obtained using QPatch16×. The external solution was (in mM): NaCl, 128; KCl, 5; MgCl$_2$, 2; CaCl$_2$, 2; Glucose, 30; HEPES, 15; pH 7.3, 305-315 mOsm. Following seal formation and whole-cell access using internal solution (containing in mM: CsF, 135; EGTA/CsOH, 1/5; HEPES 10; NaCl, 10; pH 7.3, 310-320 mOsM), voltage pulse protocols were applied. Initially a steady state inactivation voltage protocol was used to determine the half-maximal voltage for steady state inactivation (V1/2 SSI). Two holding voltages were used to determine test drug inhibition: −90 mV, where most of the channels are in a closed state; and V1/2 SSI, where half of the channels are inactivated. Currents were elicited every 10 seconds by stepping to a membrane potential of 0 mV for 20 ms. Four-point cumulative concentration responses were derived by determining the peak current amplitude at each concentration of test drug over 120 second application. Curves were fitted with the Hill equation yielding pIC50 values at −90 mV and V1/2 SSI holding potentials.

| Example Number | QP Nav1.7 −90 mV pIC50 | QP Nav1.7 SSI vhalf pIC50 |
|---|---|---|
| 1 | 4.3 | 5.5 |

The invention claimed is:

1. A compound of formula (I) which is 7-methyl-2-[4-[3-(trifluoromethoxy)phenyl]-2-pyridyl]-1,7-diazaspiro[4.4]nonan-6-one:

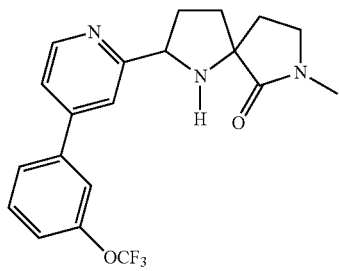

(I)

or a pharmaceutically acceptable salt thereof.

2. A compound as defined in claim 1, wherein the compound of formula (I) is a compound of any one of formulae (Ia)-(Id):

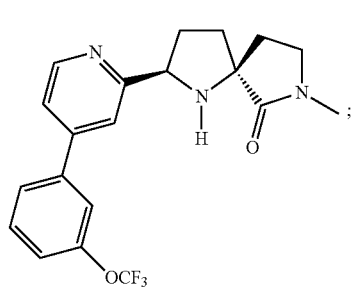

(Ia)

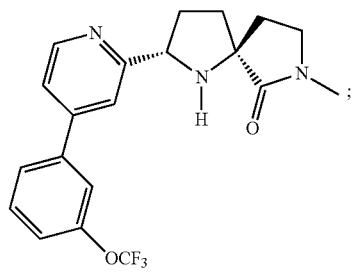

(Ib)

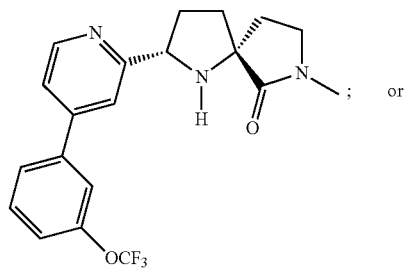

(Ic)

or

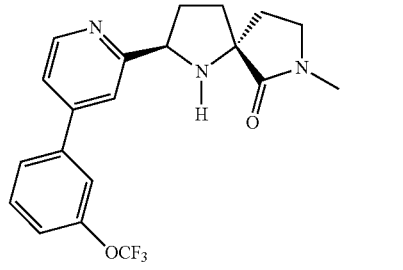

(Id)

or a pharmaceutically acceptable salt thereof.

3. A compound as defined in claim 2, wherein the compound of formula (I) is a compound of formula (Ia):

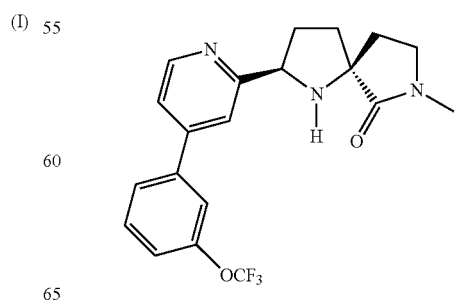

(Ia)

or a pharmaceutically acceptable salt thereof.

4. A compound of formula (I) as defined in claim 1, which is: (2R,5S)-7-Methyl-2-[4-[3-(trifluoromethoxy)phenyl]-2-pyridyl]-1,7-diazaspiro[4.4]nonan-6-one hydrochloride (E1).

5. A compound of formula (I) as defined in claim 1, which is: (2R,5S)-7-Methyl-2-[4-[3-(trifluoromethoxy)phenyl]-2-pyridyl]-1,7-diazaspiro[4.4]nonan-6-one hemisulfate (E2).

6. A compound of formula (I) as defined in claim 1, which is: (2S,5S)-7-Methyl-2-[4-[3-(trifluoromethoxy)phenyl]-2-pyridyl]-1,7-diazaspiro[4.4]nonan-6-one hydrochloride (E3).

7. A pharmaceutical composition comprising a compound of formula (I) as defined in claim 1 or a pharmaceutically acceptable salt thereof with one or more pharmaceutically acceptable carrier(s), diluents(s) and/or excipient(s).

\* \* \* \* \*